(12) United States Patent
Mori et al.

(10) Patent No.: US 8,496,807 B2
(45) Date of Patent: Jul. 30, 2013

(54) HEMODIALYSIS APPARATUS AND METHOD FOR HEMODIALYSIS

(75) Inventors: Yoshihiro Mori, Makinohara (JP); Masahiro Toyoda, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 462 days.

(21) Appl. No.: 11/556,790

(22) Filed: Nov. 6, 2006

(65) Prior Publication Data
US 2007/0108129 A1 May 17, 2007

(30) Foreign Application Priority Data

Nov. 11, 2005 (JP) ................................. 2005-327437

(51) Int. Cl.
*B01D 35/00* (2006.01)
*B01D 35/14* (2006.01)
(52) U.S. Cl.
USPC ........... 210/86; 210/85; 210/96.2; 210/321.6; 210/646; 210/739; 600/562; 604/5.01
(58) Field of Classification Search
USPC ............................................ 210/646; 356/39
See application file for complete search history.

(56) References Cited

U.S. PATENT DOCUMENTS

| 5,938,938 | A | 8/1999 | Bosetto | |
|---|---|---|---|---|
| 2003/0120170 | A1* | 6/2003 | Zhu et al. | 600/547 |
| 2004/0057037 | A1* | 3/2004 | Ohishi et al. | 356/39 |
| 2005/0102165 | A1* | 5/2005 | Oshita et al. | 705/3 |
| 2006/0043007 | A1* | 3/2006 | Tarumi et al. | 210/96.2 |
| 2006/0226079 | A1* | 10/2006 | Mori et al. | 210/646 |

FOREIGN PATENT DOCUMENTS

| EP | 1 955 723 | 10/2006 |
|---|---|---|
| JP | 2004/049492 | 2/2004 |
| JP | 2004-97781 A | 4/2004 |

OTHER PUBLICATIONS

Patent Abstracts of Japan for JP2004-097781 published Apr. 2, 2004.
Kaoru Tabei, et al., Significance of total protein concentration by water removal during hemodialysis, Division of Nephrology, Oomiya Medical Center, Jichi Medical School; 32(7) pp. 1071-1077, 1999.

* cited by examiner

*Primary Examiner* — Dirk Bass
(74) *Attorney, Agent, or Firm* — McDermott Will & Emery LLP

(57) ABSTRACT

A hemodialysis apparatus includes a dialysis device, a detecting device, an evaluation device and a memory device. The dialysis device dialyzes and ultrafiltrates blood of a patient according to an ultrafiltration volume based on an estimated dry weight while performing hemodialysis treatment on the blood circulating extracorporeally. The detecting device obtains time series data by measuring a parameter related to concentration of the blood circulating extracorporeally at a plurality of points in time series in a process of the hemodialysis treatment by the dialysis device. The evaluation device evaluates appropriateness of the hemodialysis treatment by evaluating whether the estimated dry weight approximates to a dry weight after the hemodialysis treatment by the dialysis device. The memory device stores a plurality of time series data when the hemodialysis treatment is evaluated to be appropriate by the evaluation device.

10 Claims, 5 Drawing Sheets

HEMODIALYSIS APPARATUS AND METHOD FOR HEMODIALYSIS

INCORPORATION BY REFERENCE

The present application claims priority under 35 U.S.C. §119 to Japanese Patent Application No. 2005-327437 filed on Nov. 11, 2005. The content of the application is incorporated herein by reference in its entirety.

FIELD OF THE INVENTION

The present invention relates to a hemodialysis apparatus and method which can perform hemodialysis and ultrafiltration by extracorporeally circulating blood of a patient.

BACKGROUND OF THE INVENTION

In hemodialysis treatment, a conventional hemodialysis apparatus includes a blood circuit to extracorporeally circulate blood of a patient, a dialyzer provided at the blood circuit, a peristaltic blood pump, and a dialysis device. The dialysis device allows dialysate to flow in and out to the dialyzer from the dialysis device to perform hemodialysis and ultrafiltration. The blood circuit is provided with an arterial blood circuit having an arterial needle at an end thereof and a venous blood circuit having a venous needle at an end thereof.

When the arterial needle and the venous needle are inserted to the patient, and the blood pump is turned on, blood of the patient flows through the arterial needle into the arterial blood circuit, the dialyzer, and the venous blood circuit in sequence, and then flows back into the body of the patient through the venous needle. The dialyzer includes hollow fibers forming membranes for hemodialysis. The blood flows inside of the hollow fibers. The dialysate, which has a predetermined concentration and is supplied from the dialysis device, flows outside the hollow fibers (i.e., between outside surfaces of the hollow fibers and an inside surface of a case of the dialysis device). Waste products in the blood flowing in the inside of the hollow fibers permeate into the dialysate through the membranes.

The blood flows back to the body of the patient after flowing through the venous blood circuit and after the waste products being removed from the blood. Also, the dialysis device is provided with an ultrafiltration pump that removes water from the blood. The blood is also ultrafiltrated through the membranes during the hemodialysis treatment. A volume of water to be ultrafiltrated by the ultrafiltration pump (i.e., an ultrafiltration rate) is adjusted by controlling a driving rate of the ultrafiltration pump.

However, if the volume of water to be ultrafiltrated (the ultrafiltration volume) is large, it is necessary to increase the ultrafiltration rate, and the patient may develop shock syndromes such as hypotension depending on the health condition of the patient. To detect the predictor of such shock syndromes, a device has been proposed to measure a hematocrit value (red blood cell volume ratio in blood) and monitor the patient by calculating a variation rate of a circulating blood volume ($\Delta BV$) from the hematocrit value.

Normally, the variation rate of the circulating blood volume ($\Delta BV$) becomes lower with the time course of treatment, but when drastic drop of $\Delta BV$ occurs, it is regarded as the predictor of shock syndromes such as hypotension. However, it is possible to prevent shock syndromes to occur by applying some treatments (fluid replacement, terminating hemodialysis, and the like) at the time of the drastic drop of $\Delta BV$. Thus, an apparatus for hemodialysis is disclosed, for example, in Japanese Laid-Open Patent Publication No. 2004-977811 that measures hematocrit values of a patient sequentially and calculates the variation rate of the circulating blood volume ($\Delta BV$) of the patient from these hematocrit values.

An ultrafiltration volume controlled by the ultrafiltration pump described above is to be set so as to make a body weight of the patient close to a dry-weight of the patient (body weight of the patient when a volume of an interstitial fluid outside of cells is properly adjusted). The dry-weight of the patient is estimated based on experiences of a medical staff, such as a medical doctor (the dry weight obtained in such a way is called "the estimated dry weight"), and the ultrafiltration volume is to be set so as to be the estimated dry weight. The nearness of the estimated dry weight to the true dry weight (called dry weight) can be grasped by whether PWI (Plasma Water Index), which is obtained by a formula dividing a variation rate of a circulating blood plasma volume ($\Delta CPV$ %) by a variation rate of body weight ($\Delta BW$ %), is within a predetermined range.

However, the conventional hemodialysis apparatus as described above has the following problems.

Although the conventional hemodialysis apparatus as described above can evaluate whether the hemodialysis treatment has been appropriate with the estimated dry weight approximating to the dry weight based on PWI, the appropriateness of the treatment can only be evaluated after the treatment is completed because the proper value of PWI may vary over time or depending on the dialysis condition. Thus, it can not be evaluated whether the hemodialysis treatment is proceeding properly with the estimated dry weight approximating to the dry weight.

On the other hand, it has been known in a stable patient undergoing hemodialysis treatment for relatively long term that time series data (especially standardized data) are reproducible when they are obtained by measuring parameters such as the variation rate of the circulating blood volume, $\Delta BV$, which relate to the concentration of blood circulating extracorporeally, in time series at a plurality of points during hemodialysis treatment process. Thus, the present applicants investigated a hemodialysis apparatus which can grasp the appropriateness of hemodialysis treatment during the course of treatment in real time by taking advantage of the reproducibility of time series data.

The present invention is achieved by taking this situation into consideration and provides an apparatus and method for hemodialysis by which a plurality of the courses (time series data) for appropriate hemodialysis treatments are stored where the estimated dry weight approximates to the dry weight, and in which, in the hemodialysis treatments thereafter, it is easy to evaluate whether the hemodialysis treatment is following the course in which the treatment would produce an appropriate result approaching the dry weight.

SUMMARY OF THE INVENTION

According to one aspect of the present invention, a hemodialysis apparatus includes a dialysis device that dialyzes and ultrafiltrates blood according to an ultrafiltration volume based on an estimated dry weight while performing dialysis on blood of a patient circulating extracorporeally to perform hemodialysis, a detecting device by which time series data are obtained by measuring a parameter related to concentration of the blood circulating extracorporeally at a plurality of points in time series in a process of hemodialysis treatment by the dialysis device, an evaluation device that evaluates appropriateness of the hemodialysis treatment by evaluating whether the estimated dry weight approximates to a dry weight after the hemodialysis treatment by the dialysis device, and a memory device that can store a plurality of time series data when the hemodialysis treatment is evaluated to be appropriate by the evaluation device.

According to another aspect of the present invention, the evaluation device evaluates whether the aforementioned estimated dry weight approximates to the dry weight based on calculating an index called PWI.

According to yet another aspect of the present invention, the aforementioned hemodialysis apparatus further includes a calculation device for calculating optimal change in time series data expected in an appropriate process of hemodialysis treatment based on a plurality of time-series data stored in the memory device.

According to yet another aspect of the present invention, the aforementioned calculation device calculates an optimal range of change with a predetermined range between the lower limit and the upper limit at each measuring point of a parameter related to the concentration of the blood circulating extracorporeally.

According to yet another aspect of the present invention, a parameter measured by the aforementioned detecting device is displayed in real time superimposed on a graph, by which the optimal change or range of change calculated by the aforementioned calculation device is displayed, when hemodialysis treatment is performed by the aforementioned dialysis device.

According to yet another aspect of the present invention, wherein a predetermined notification is provided on condition that a parameter measured by the aforementioned detecting device deviates from the optimal change or range of change calculated by the aforementioned calculation device when hemodialysis treatment is performed by the aforementioned dialysis device.

According to yet another aspect of the present invention, wherein the time series data stored in the aforementioned memory device are standardized by performing a predetermined operation to convert them to universal time series data unrelated to a particular patient's specific conditions such as body weight and ultrafiltration volume of the patient.

According to yet another aspect of the present invention, a parameter measured by the aforementioned detecting device is a variation rate of a circulating blood volume ($\Delta BV$) calculated from the concentration of the blood circulating extracorporeally.

According to yet another aspect of the present invention, a method for hemodialysis including the steps of performing hemodialysis treatment by ultrafiltration according to an ultrafiltration volume based on an estimated dry weight while performing hemodialysis treatment on the blood of a patient circulating extracorporeally, obtaining time series data by evaluating a parameter related to concentration of the blood circulating extracorporeally at a plurality of points in time series during hemodialysis treatment by the dialysis device, evaluating, after the hemodialysis treatment, appropriateness of this hemodialysis treatment by evaluating whether the aforementioned estimated dry weight approximates to the dry weight, and storing a plurality of time series data that are evaluated to be optimal.

According to yet another aspect of the present invention, in the aforementioned method, it is evaluated whether the aforementioned estimated dry weight approximates to the dry weight based on calculating an index called PWI.

According to yet another aspect of the present invention, in the aforementioned method for hemodialysis, an optimal change in time series data, which are expected during the course of an appropriate hemodialysis treatment, are calculated based on a plurality of stored time series data.

According to yet another aspect of the present invention, in the aforementioned method for hemodialysis, calculation is performed to obtain an optimal range of change having a predetermined range between the lower limit and the upper limit at each measuring point of a parameter related to the concentration of the blood circulating extracorporeally.

According to yet another aspect of the present invention, in the aforementioned method for hemodialysis, a measured parameter is displayed in real time superimposed on a graph, by which the calculated optimal change or range of change is displayed, when hemodialysis treatment is performed.

According to yet another aspect of the present invention, in the aforementioned method for hemodialysis, a predetermined notification is provided on condition that a measured parameter deviates from the calculated optimal change or range of change when hemodialysis treatment is performed.

According to yet another aspect of the present invention, in the method for hemodialysis, the stored time series data are standardized by performing a predetermined operation to convert them to universal time series data unrelated to a particular patient's specific conditions such as body weight and ultrafiltration volume of the patient.

According to yet another aspect of the present invention, in the aforementioned method for hemodialysis, a measured parameter is a variation rate of a circulating blood volume ($\Delta BV$) calculated from a concentration of blood circulating extracorporeally.

Because appropriateness of this hemodialysis treatment is evaluated, after the hemodialysis treatment, by evaluating whether the estimated dry weight approximates to the dry weight, and a plurality of time series data, which are evaluated to be optimal, are stored according to one aspect of the present invention, it is easy to evaluate whether the hemodialysis treatment is following the course in which the treatment would produce an appropriate result approaching the dry weigh.

Because it is evaluated based on calculating an index called PWI whether the aforementioned estimated dry weight approximates to the dry weight according to another aspect of the present invention, the appropriateness of the hemodialysis treatment can be determined by evaluating more simply and reliably whether the estimated dry weight approximates to the dry weight.

Because an optimal change in time series data, which are expected during the course of an appropriate hemodialysis treatment, are calculated based on a plurality of stored time series data according to yet another aspect of the present invention, evaluation whether the estimated dry weight approximates to the dry weight can be made more easily by comparing such an optimal change and a parameter (parameter related to concentration of the blood circulating extracorporeally).

Because calculation is performed to obtain an optimal range of change having a predetermined range between the lower limit and the upper limit at each measuring point of a parameter related to the concentration of the blood circulating extracorporeally according to yet another aspect of the present invention, it can be seen whether the parameter (related to the concentration of the blood circulating extracorporeally) that is measured in the process of hemodialysis treatment thereafter is within this optimal range.

Because a measured parameter is displayed in real time superimposed on a graph, by which the calculated optimal change or range of change is displayed, when hemodialysis treatment is performed according to yet another aspect of the present invention, the evaluation can be made visually whether the estimated dry weight approximates to the dry weight in the optimal process during the hemodialysis treatment, as well as a sign can be noticed that the measured parameter exceeds the upper or lower limit.

Because a predetermined notification is provided on condition that a measured parameter deviates from the calculated optimal change or range of change when hemodialysis treatment is performed according to yet another aspect of the present invention, medical staffs may be warned.

Because the stored time series data are standardized by performing a predetermined operation to convert them to universal time series data unrelated to a particular patient's specific conditions such as body weight and ultrafiltration volume of the patient according to yet another aspect of the present invention, the evaluation can be made whether the estimated dry weight approximates to the dry weight in the optimal process, based on the time series data of not only the specific patients but also many patients receiving hemodialysis treatment. Also, even if the evaluation is only applied to the specific patients whether the estimated dry weight approximates to the dry weight in the optimal process, the change in the pretreatment body weigh of the patient, the ultrafiltration volume and the like, which may be different in each hemodialysis treatment, will not influence the evaluation.

Because a measured parameter is a variation rate of a circulating blood volume (ΔBV) calculated from a concentration of blood circulating extracorporeally according to yet another aspect of the present invention, the evaluation can be made easily whether the estimated dry weight approximates to the dry weight in the optimal process of the variation rate of a circulating blood volume in the course of a hemodialysis treatment.

DESCRIPTION OF THE EMBODIMENTS

The embodiments of the present invention will now be described in particular with reference to the accompanying drawings.

Figure 1:
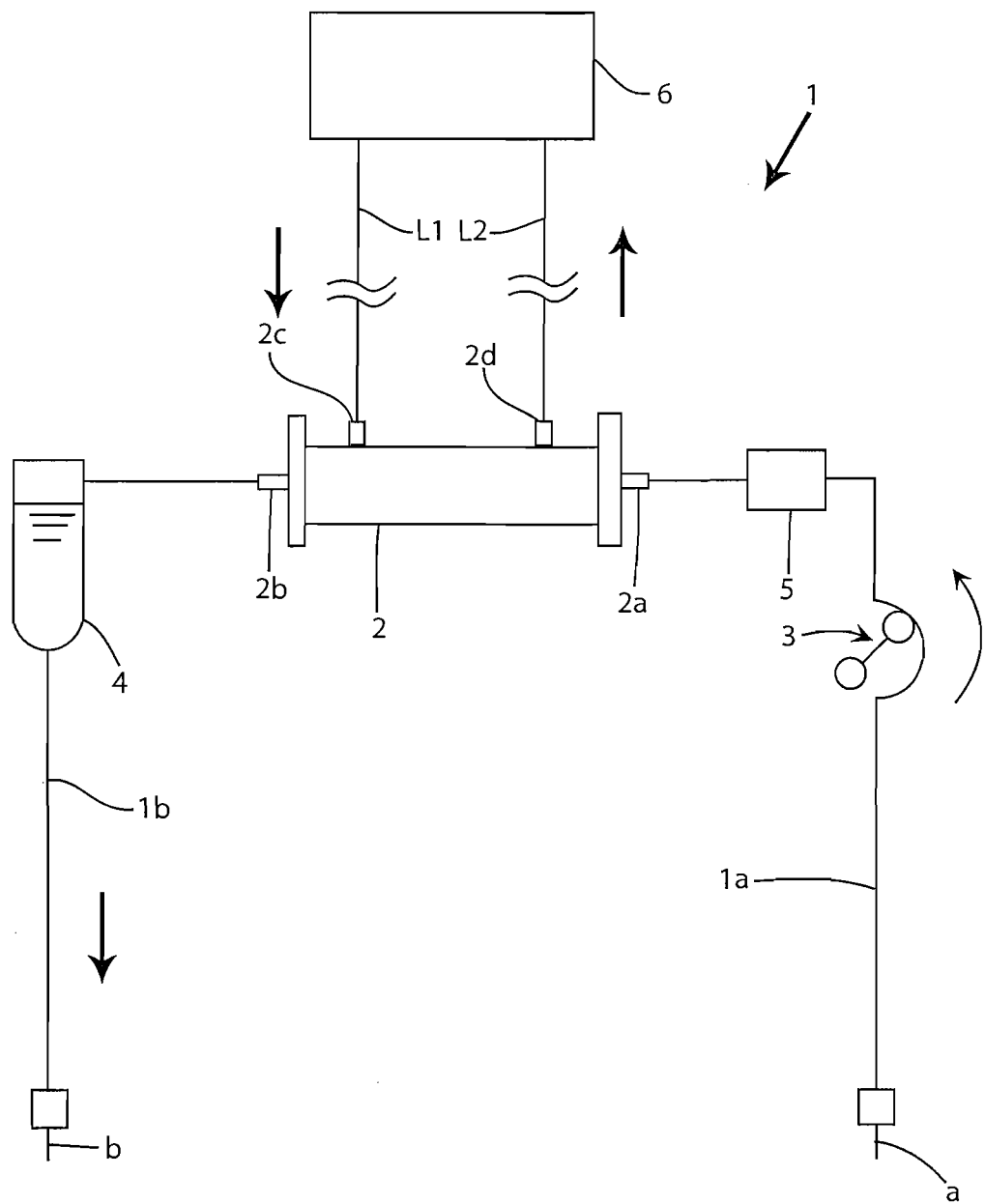
FIG. 1 is a schematic diagram of a hemodialysis apparatus of the present invention.

A hemodialysis apparatus according to the present embodiment is used to perform hemodialysis and ultrafiltration by extracorporeally circulating blood of a patient. As shown in FIG. 1, the hemodialysis apparatus includes a blood circuit 1 to circulate extracorporeally blood of the patient, a dialyzer 2 that is connected to the blood circuit and performs hemodialysis treatment and a dialysis device 6 that is connected to the dialyzer 2 and ultrafiltrates while supplying dialysate. Further, as shown in FIG. 1, the blood circuit 1 is provided with an arterial blood circuit 1a and a venous blood circuit 1b each made from flexible tubing, and the dialyzer 2 is connected between these arterial blood circuit 1a and venous blood circuit 1b.

The arterial blood circuit 1a is provided at an end thereof with an arterial needle a, and also provided therealong with a blood pump 3 and a hematocrit sensor 5. The venous blood circuit 1b is provided at an end thereof with a venous needle b, and also provided therealong with a drip chamber 4 to remove bubbles.

The hematocrit sensor 5 has a photo emitter (e.g., a light emitting diode) and a photo detector (e.g., a photo diode), and measures a hematocrit value indicating a concentration of the blood of the patient that circulate extracorporeally in the blood circuit 1. The hematocrit sensor 5 can function by emitting a light with a predetermined wavelength to the blood from the photo emitter and detecting either a transmitted or reflected light by the photo detector. Specifically, the hematocrit value is an index indicating a concentration of the blood, in particular a ratio of a volume of red blood cells to the total volume of blood.

When the blood pump 3 is turned on while the arterial needle a and the venous needle b are inserted to the patient, the blood of the patient flows through the arterial blood circuit 1a into the dialyzer 2 that dialyzes the blood. Subsequently, the blood returns to the body of the patient through the venous blood circuit 1b after bubbles are removed by the drip chamber 4. Thus, the blood is dialyzed by the dialyzer 2 during extracorporeal circulation through the blood circuit 1.

The dialyzer 2 is provided on its case with a blood inlet port 2a, a blood outlet port 2b, a dialysate inlet port 2c and a dialysate outlet port 2d. The blood inlet port 2a and the blood outlet port 2b are each connected to ends of the arterial blood circuit 1a and the venous blood circuit 1b, respectively. Additionally, a dialysate inlet line L1 and a dialysate outlet line L2 are each extended from the dialysis device 6, and each connected to the dialysate inlet port 2c and the dialysate outlet port 2d, respectively.

The dialyzer 2 includes a plurality of hollow fibers. The blood flows through the inside of the hollow fibers, and the dialysate flows between outside surfaces of the hollow fibers and an inside surface of a case of the dialyzer 2. The hollow fibers are provided with a plurality of micropores on the inside and outside surfaces of the hollow fibers. This forms permeable membranes which allow waste products in the blood to permeate into the dialysate.

Figure 2:
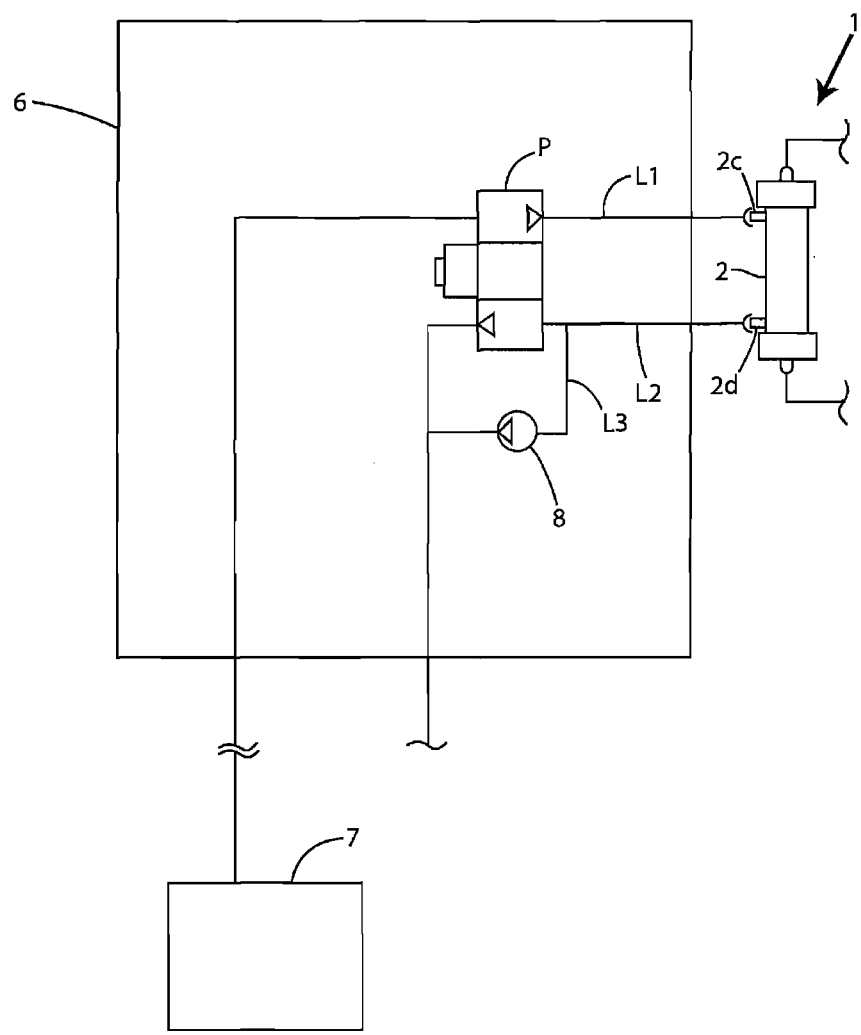
FIG. 2 is a schematic diagram of a dialysis device in the hemodialysis apparatus of the present invention, showing a mechanical structure of the dialysis device.

As shown in FIG. 2, the dialysis device 6 includes a duplex pump P, a bypass line L3 and an ultrafiltration pump 8. The duplex pump P is connected to both the dialysate inlet line L1 and the dialysate outlet line L2, bridging those two lines L1 and L2. The bypass line L3 is connected to the dialysate inlet line L2 bypassing the duplex pump P, and is also connected to the ultrafiltration pump 8. The dialysate inlet line L1 is connected at one end thereof to the dialysate inlet port 2c of the dialyzer 2, and at another end thereof to a dialysate supplying device 7 that prepares the dialysate of a predetermined concentration.

The dialysate outlet line L2 is connected at one end thereof to the dialysate outlet port 2d of the dialyzer 2, and at another end thereof to a fluid disposal device (not shown). The dialysate supplied from the dialysate supplying device 7 flows through the dialysate inlet line L1 into the dialyzer 2, then, flows through the dialysate outlet line L2 and the bypass line L3 into the fluid disposal device.

The ultrafiltration pump 8 ultrafiltrates the blood of the patient flowing in the dialyzer 2 removing water. When the ultrafiltration pump 8 is activated, a volume of the dialysate flowing out from the dialysate outlet line L2 becomes greater than a volume of the dialysate flowing in through the dialysate inlet line L1 because the duplex pump P is a metering pump. Accordingly, water is removed from the blood by the difference between the volumes flowing out and flowing in. Devices other than the ultrafiltration pump 8 (e.g., a balancing chamber) may be used to ultrafiltrate the blood. Further, the duplex pump P and the ultrafiltration pump 8 together form a dialyzing device, which performs the hemodialysis and the ultrafiltration by extracorporeally circulating the blood of the patient.

While medical staff such as physicians set an ultrafiltration volume based on an estimated dry weight before starting hemodialysis treatment, and the ultrafiltration pump 8 is driven based on such ultrafiltration volume. Here, the estimated dry weight is based on the past examination and experience of the medical staff and is not necessarily the same as the dry weight.

Figure 3:
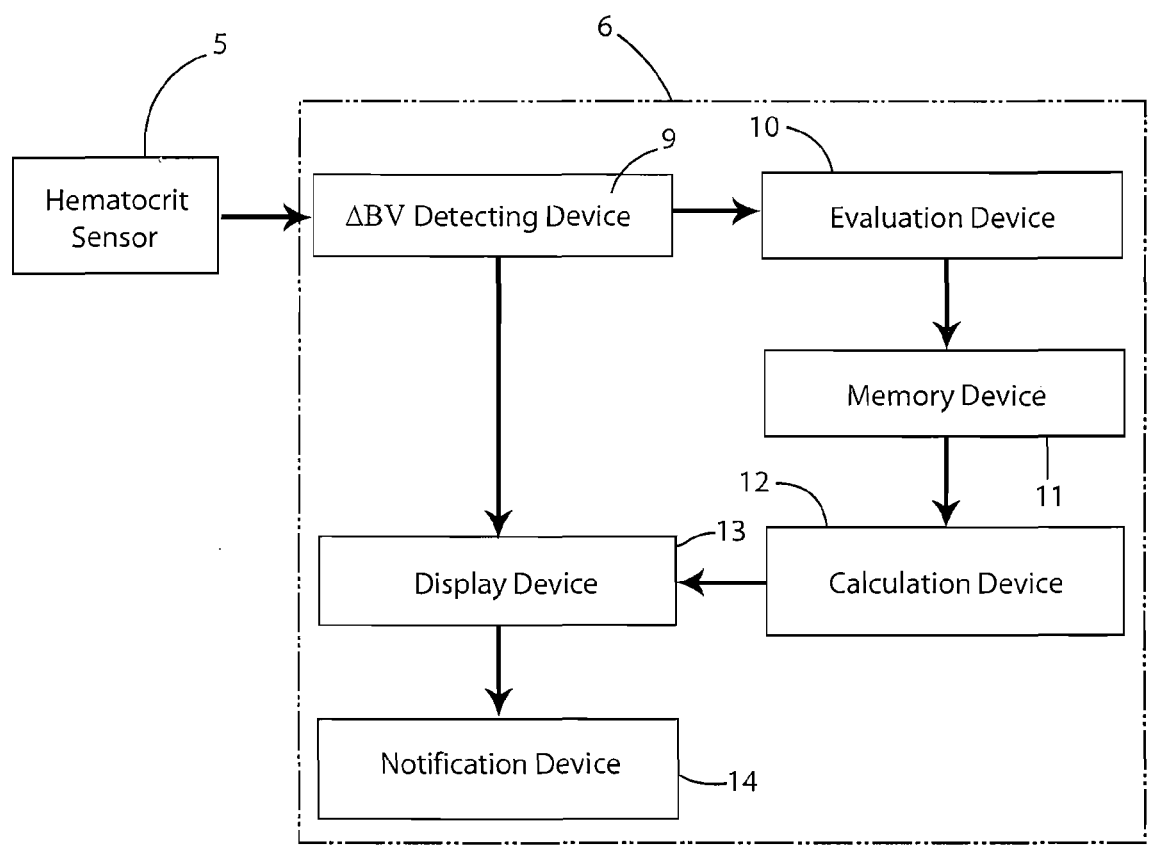
FIG. 3 is a block diagram of a dialysis device in the hemodialysis apparatus of the present invention, showing a electric structure of the dialysis device.

As shown in FIG. 3, the dialysis apparatus 6 is provided with a detecting device of the present invention, that is a ΔBV detecting device 9, an evaluation device 10, a memory device 11, a calculation device 12, a display device 13 including a display and the like provided on the dialysis apparatus 6, a notification device 14 including a speaker capable of voice output. The ΔBV detecting device 9 is connected electrically with the hematocrit sensor 5, and calculates and measures a variation rate of a circulating blood volume (ΔBV) based on this hematocrit value outputted by this hematocrit sensor 5.

The time series data (data indicating the trend of circulating blood volume rate with the passage of time) measured at a plurality of points in time series can be obtained by measuring successively a parameter related to the concentration of the blood circulating extracorporeally (i.e. hematocrit value) with the hematocrit sensor 5 and also by measuring the variation rate of the circulating blood volume (ΔBV) with the ΔBV detecting device 9.

In this regard, the variation rate of the circulating blood volume, ΔBV, may be obtained from a formula ΔBV=(Ht value at the starting time of dialysis−Ht at measuring time)/Ht at measuring time×100 where Ht is a hematocrit value obtained by the hematocrit sensor 5. Using this formula, the variation rate of the circulating blood volume (ΔBV) of a patient can be measured sequentially in the passage of time of the hemodialysis treatment, and the time series data of this hemodialysis treatment can be obtained.

The ΔBV detecting device 9 described above calculates the variation rate of the circulating blood volume (ΔBV %) based on a measured hematocrit value. Instead, the variation rate of the circulating blood volume (ΔBV %) may also be calculated based on a hemoglobin concentration, a total protein concentration of the serum and the like. Further, on measuring a parameter for calculating the variation rate of the circulating blood volume (ΔBV %), various devices such as optical, ultrasonic and the like may be used.

The evaluation device 10 is to evaluate the appropriateness of this hemodialysis treatment by evaluating whether the estimated dry weight approximates to the dry weight after the hemodialysis treatment. The evaluation device is electrically connected with the ΔBV detecting device 9 and the memory device 11. PWI (plasma water index) may be used as a evaluating criteria for the estimated dry weight in the evaluation device 10. The PWI is an index for the effect of the change (decrease) in body weight by the ultrafiltration on the blood concentration. The PWI is calculated by dividing a variation rate of a circulating blood plasma volume (ΔCPV %) with the variation rate of the body weight (ΔBW %) of a patient according to the formula (PWI=ΔCPV %/ΔBW %). It has been indicated that the value of PWI is in the optimal range if the estimated dry weight approximates to the dry weight.

A larger PWI value indicates a larger blood concentration rate for the reduction of the body weight by the ultrafiltration suggesting that the loss of water by the ultrafiltration is not compensated with an interstitial fluid from outside of the blood vessel. On the other hand, a smaller PWI is considered that ample interstitial fluid is supplied even if water is removed from the blood.

Further, parameters to obtain PWI, ΔBW(%) and ΔCPV (%) may be calculated as follows. The variation rate of the body weight, ΔBW(%) may be obtained using Formula 1 below and the ultrafiltration volume (total ultrafilterated volume at the end of the hemodialysis treatment: UFV), which is obtained from the body weight of a patient before the hemodialysis treatment (BW1) and a driving rate of the ultrafiltration pump 8.

$$\Delta BW\% = \qquad \text{(Formula 1)}$$
$$(BW2 - BW1)/BW1 \times 100(\%) = (-UFV)/BW1 \times 100(\%)$$

Here, BW2 is the body weight of the patient at the end of the hemodialysis treatment. An increase or decrease due to eating, drinking, excretion and the like is not taken into consideration.

Still further, the variation rate of the circulating blood plasma volume (ΔCPV %) (variation rate of blood index) may be obtained using formula 2 described below, and a hematocrit value at the start of the ultrafitration (Ht1(%)) and a hematocrit value at the end of ultrafiltration (Ht2(%)) measured by the hematocrit sensor 5. When CPV1 and BV1 are a circulating blood plasma volume and a circulating blood volume at the start of ultrafiltration, respectively, and CPV2 and BV2 are a circulating blood plasma volume and a circulating blood volume at the end of ultrafiltration, respectively, and because blood plasma volume=blood volume×(1-red blood cell volume ratio), then CPV1=BV1×(1−Ht1/100), and CPV2=BV2×(1−Ht2/100).

$$\Delta CPV \% = (CPV2 - CPV1)/CPV1 \times 100 =$$
$$\{BV2(1 - Ht2/100) - BV1(1 - Ht1/100))/(BV1(1 - Ht1/100)\} \times$$
$$100 = (BV2 - BV1 - BV2 \times Ht2/100 + BV1 \times Ht1/100)/$$
$$\{BV1(1 - Ht1/100)\} \times 100$$

Because red blood cells in circulating blood are not lost and the volume does not vary during the hemodialysis treatment, the formula BV1×Ht1=BV2×Ht2 (both sides of the formula are ratios of red blood cell volume in circulating blood volume) is satisfied.

Therefore, the following formula is satisfied.

$$\Delta CPV \% = (BV2 - BV1)/\{BV1(1 - Ht1/100)\} \times 100 = \qquad \text{(Formula 2)}$$
$$(BV2/BV1 - 1)/(1 - HT1/100) \times 100 =$$
$$(Ht1/Ht2 - 1)/(1 - Ht1/100) \times 100(\%)$$

In place of the criteria for the estimated dry weight based on PWI as described above, a cardiothoracic ratio may be used as a criterion. The cardiothoracic ratio is a ratio of the length of the thorax (width) to the size of the heart (width) in the chest X ray photograph of the patient. The dry weight is defined as the body weight when the cardiothoracic ratio is 50% or below. Thus, it can be evaluated whether the estimated dry weight approximates to the dry weight by the cardiothoracic ratio measured after the hemodialysis treatment. Also, the approximation of the estimated dry weight to the dry weight may be evaluated by, in addition to the PWI and cardiothoracic ratio described above, considering the blood pressure of a patient, factors specific for individual patient, sex, primary disease and the like. The memory device 11 includes a memory and the like and is capable of storing only a plurality of time series data from the hemodialysis treatments which have been evaluated by the evaluation device 10 to be appropriate. Because the time series data are sequentially stored when the evaluation device 10 evaluates that the patient's PWI is in the optimal range after the hemodialysis treatment, only the time series data in the optimal hemodialysis treatment where the estimated dry weight approximates to the dry weight are stored cumulatively in the memory device 11.

Figure 4:
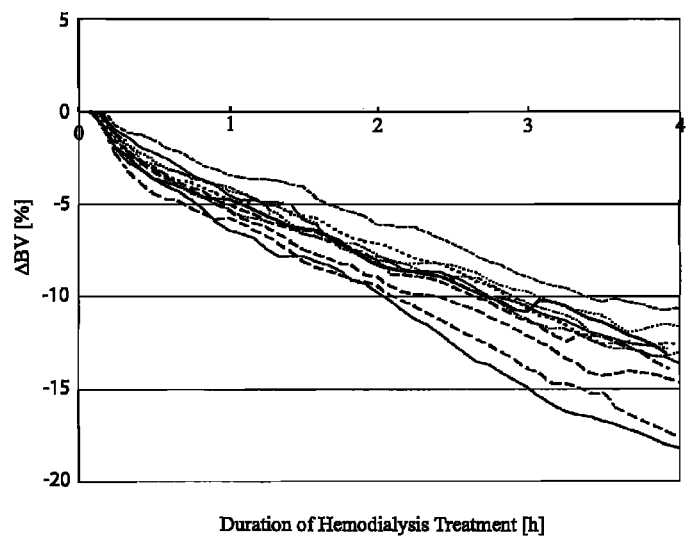
FIG. 4 is a graph of a plurality of time series data stored by a memory device in the hemodialysis apparatus of the present invention displayed by a display device.

For example, FIG. 4 shows a graph of a plurality of time series data of one patient stored in the memory device 11. In this graph, time series data of hemodialysis treatments in a plurality of days are shown, and the horizontal axis indicates the duration of hemodialysis treatment (h) and the vertical axis indicates the variant ratio of the circulating blood volume, $\Delta BV(\%)$ measured by the $\Delta BV$ detecting device 9. The pretreatment body weight (the body weight of a patient before the hemodialysis treatment) is varied in each day of the hemodialysis treatment.

The calculation device 12 calculates the optimal change of the predicted time series data in the process of optimal hemodialysis treatment, based on a plurality of time series data stored in the memory device 11 (e.g. data shown as a plurality of graphs in FIG. 4). The calculation device 12 is also organized to calculate the optimal change after performing a predetermined operation on the time series data stored in the memory device 11 and standardizing them to convert to universal time series data unrelated to a particular patient's specific conditions such as body weight and ultrafiltration volume of the patient.

The standardization of the time series data may be performed by the calculation dividing $\Delta BV$ value (variable) obtained by the hemodialysis treatment with the variation rate of the body weight before and after the hemodialysis treatment ($\Delta BW\ \%$) ($\Delta BV$/final $\Delta BW$). This variation rate of the body weight ($\Delta BW\ \%$) can be calculated by Formula 1 described above. In particular, the standardized and universal time series data, which are unrelated to a particular patient's specific conditions such as body weight and ultrafiltration volume of the patient (e.g. the graph in FIG. 5), can be obtained by substituting the target ultrafiltration volume of the hemodialysis treatment (optimal hemodialysis treatment) and the pretreatment body weight of the patient (the body weight before the hemodialysis treatment) to the terms of accumulated ultrafiltration volume (UFV) and pretreatment body weight (BW1) in this Formula 1, respectively.

Figure 5:
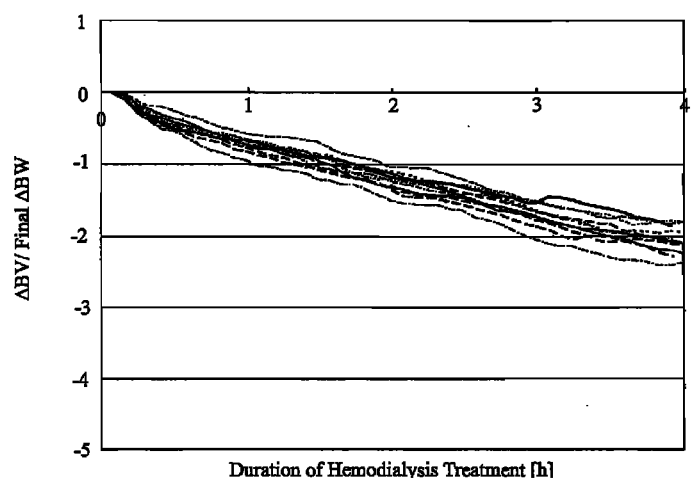
FIG. 5 is a graph of a plurality of standardized time series data stored in a memory device in the hemodialysis apparatus of the present invention displayed by a display device.

However, for easy visualization of the comparison with non-standardized graphs, in FIG. 5 (also in FIG. 7) the results of the calculation are shown as graphs using the decreasing rate of the body weight, which is a positive value, in lieu of the variation rate of the body weight $\Delta BW\ \%$, which is a negative value. Because the variation rate of body weight, $\Delta BW\ \%$, is a negative value, the decreasing rate of body weight is expressed "$-\Delta BW\ \%$." As the result the graphs go downward with the passage of time. Further, the calculation for the standardization of such time series data may be performed by an outside device which is different from the calculation device 12.

According to the graph of FIG. 5, the standardized time series data described above during the optimal hemodialysis treatment, in which the estimated dry weight approximates to the dry weight, shows almost the same change in the passage of time (trend). To these standardized time series data, a curvilinear regression analysis may be applied (i.e. to find a correlation), and the optimal change of the time series data expected during the optimal hemodialysis treatment may be calculated.

Figure 6:
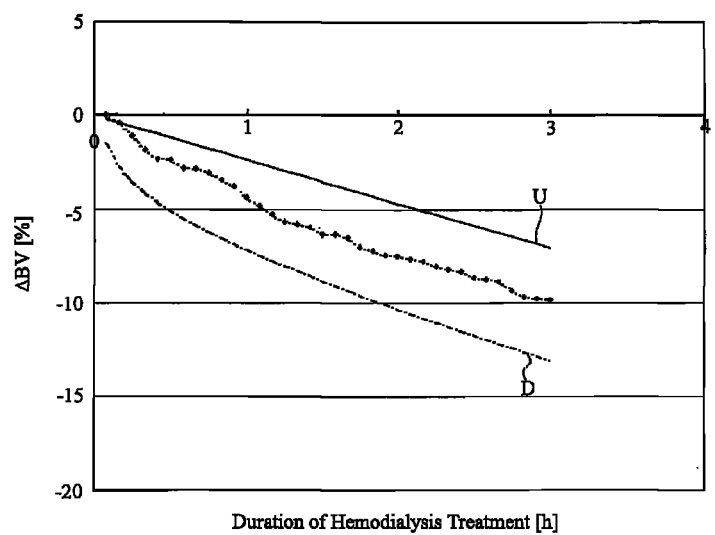
FIG. 6 is a graph of the optimal range calculated by a calculation device in the hemodialysis apparatus of the present invention, displayed superimposed by a display device on a variation rate of a circulating blood volume (ΔBV) measured in the process of a hemodialysis treatment by a ΔBV detecting device.

Also, an optimal range with predetermined lower and upper limit may be calculated at each measuring point (each measuring point of a parameter related to the concentration of extracorporeally circulating blood ($\Delta BV$ in the present embodiment) from the distribution of the standardized time series data. For example, the upper limit value function (U) and lower limit value function (D) of the passage of time of hemodialysis treatment may be obtained, as shown in FIG. 6, from a graph of the optimal variation range by making the upper and lower limit values as the functions of the time of hemodialysis treatment.

Further, the change of the blood index in the hemodialysis treatment may be predicted using the regression curve standardized as described above and by substituting the target volume of ultrafiltration of the hemodialysis treatment to be performed and the pre-treatment body weight of the patient to this regression curve. Because $\Delta BV$/final $\Delta BW = \Delta BV(\%)$/ (ultrafiltrated volume/pre-treatment $BW \times 100(\%)$), the change of $\Delta BV$ may be predicted by substituting the terms "ultrafiltrated volume" and "pre-treatment BW" with "Target ultrafiltrated volume" of the hemodialysis treatment and the body weight of the patient measured before the hemodialysis treatment (pre-treatment body weight), respectively.

Further, the range of $\Delta BV$ (upper and lower limit values) at time t in the hemodialysis treatment may be predicted from the upper and lower limit value function to the hemodialysis treatment time by substituting the term of the final BW with pre-treatment body weight and the target ultrafiltration volume as described above.

The predicted change obtained as described above may be compared with the trend of the optimal change by displaying on the display device 13 described below. However, when the predicted change is different from the optimal change, the hemodialysis treatment condition may be changed to correct the difference.

The display device 13 displays the variation rate of the circulating blood volume ($\Delta BV$) measured by the $\Delta BV$ detecting device 9 in real time superimposed on a graph, by which the optimal change or range of change calculated by the calculation device 12 is displayed, when hemodialysis treatment is performed by the hemodialysis apparatus of the present invention. As an example, FIG. 6 shows a graph of the measured variation rate of the circulating blood volume ($\Delta BV$) and the optimal range of change having upper and lower limit values. By this display the evaluation whether the hemodialysis treatment is proceeding properly with the estimated dry weight approximating to the dry weight may be carried out more visually and at the same time, it may be possible to catch the sign of the variation rate of the circulating blood volume ($\Delta BV$) exceeding the upper or lower limit values.

The notification device 14 provides a predetermined notification when the measured variation rate of the circulating blood volume ($\Delta BV$) deviates from the optimal change or range of change calculated by the calculation device 12. The notification device 14 includes, for example, a speaker capable of outputting voice and a light source (LED and the like) capable of emitting light. In the process of the hemodialysis treatment, if the measured variation rate of the circulating blood volume (ΔBV) exceeds the upper limit of the optimal range of change, it is evaluated that the estimated dry weight is higher than the dry weight of a patient (the pre-set ultrafiltration volume is too small), and if the ΔBV is lower than the lower limit value, it is evaluated that the estimated dry weight is lower than the dry weight of the patient (the pre-set ultrafiltration volume is too large). Thus guidance can be given according to this evaluation.

Because predetermined notification is provided during the hemodialysis treatment on condition that a measured parameter deviates from the calculated optimal change or range of change, the medical staff are properly warned. Further, the contents of the notifications and guidance by the notification device 14 may be recorded to be utilized for the hemodialysis treatments thereafter.

According to the hemodialysis apparatus described above, it is easy to evaluate whether the process of the hemodialysis treatment is appropriate with the estimated dry weight approximating to the dry weight because appropriateness of the hemodialysis treatment is evaluated based on whether the estimated dry weight approximates to a dry weight, and the memory device stores a plurality of time series data when the hemodialysis treatment is evaluated to be appropriate. Also, it is easy to evaluate whether the variation rate of the circulating blood volume (ΔBV) proceeds appropriately with the estimated dry weight approximating to the dry weight in the hemodialysis treatment because ΔBV, which is calculated from the concentration of the blood circulating extracorporeally, is measured as a parameter.

In addition, there is no need to obtain chest X-ray photographs which are needed for evaluation by cardiothoracic ratio because the evaluation whether the estimated dry weight approximates to the dry weight of a patient is based on the calculation of PWI. Therefore, the appropriateness of this hemodialysis treatment can be evaluated more simply and reliably by evaluating whether the estimated dry weight approximates to the dry weight.

Further, by comparing the optimal change and the variation rate of the circulating blood volume (ΔBV) (a parameter related to the concentration of blood circulating extracorporeally) measured in the process of the hemodialysis treatment thereafter, the evaluation whether the process is appropriate with the estimated dry weight approximating to the dry weight can be made more easily. In particular, when the optimal range of change having a predetermined width from the lower limit value to the upper limit value is calculated in each measuring point of the variation rate of the circulating blood volume (ΔBV), it can be confirmed whether the variation rate of the circulating blood volume (ΔBV) measured in the hemodialysis treatment thereafter is in the optimal range.

Still further, even if the evaluation is only applied to the specific patients whether the estimated dry weight approximates to the dry weight in the optimal process, the change in the pretreatment body weight of the patient, the ultrafiltration volume and the like, which may be different in each hemodialysis treatment, may not influence the evaluation, because the time series data stored in the memory device 11 are standardized by performing a predetermined operation to convert them to universal time series data unrelated to a particular patient's specific conditions such as body weight and ultrafiltration volume of the patient.

Figure 7:
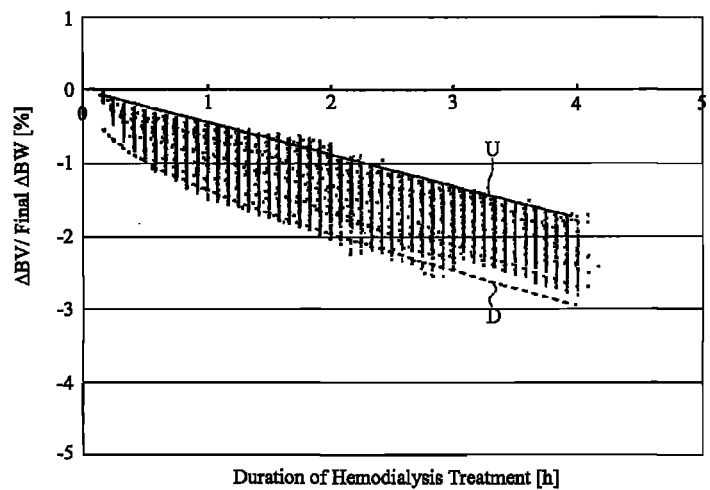
FIG. 7 is a graph showing the distribution range that is obtained by applying the regression calculation on the time series data of many patients in the hemodialysis apparatus of the present invention.

However, not only the time series data from a specific patient as described above embodiment, but also the time series data from many patients of the hemodialysis treatment may be standardized by performing the predetermined operation, and based on these time series data, the evaluation may be made whether the process is appropriate with the estimated dry weight approximates to the dry weight. In this case, as shown in FIG. 7, it is preferable to calculate the distribution range at each predetermined time by subjecting the time series data of many dialysis patients to regression calculation and the like and to obtain the optimal range of change having the standardized upper and lower limit values.

The present embodiments are described as above but the present invention is not limited to this description. For example, other parameters related to the blood concentration (the hematocrit value itself, the circulating blood volume (BV), the circulating blood plasma volume (CPV), the variation rate of circulating blood plasma volume (ΔCPV) and the like) may be measured at a plurality of time points in every time series to obtain the time series data, and it may be arranged that these time series data are evaluated by the evaluation device 10.

Further, in the process of measuring the variation rate of the circulating blood volume (ΔBV), it may be designed so that the patient can input events such as drinking and eating, fluid replacement or change of the position (turning over in bed) and eliminate (preventing the data input) the effect of apparent change in the variation rate of the circulating blood volume (ΔBV). In this case accuracy of time series data collection may be improved.

Further, the memory device which stores a plurality of the time series data of the hemodialysis treatments evaluated to be appropriate by the evaluation device is not limited to the device disposed in the hemodialysis apparatus such as the present embodiments, but for example, an outside central monitoring system may be used. In this case the time series data of patients may be placed in common use, and the common time series data of patients may be managed as a unit after converting to a data base. Still further, the optimal change or optimal range of change which is calculated by the calculation device 12 may be corrected according to the change in the dialysis condition and the opinions of the medical staff such as physicians and the like.

If the apparatus and method for hemodialysis obtain time series data by measuring parameters related to the concentration of the extracorporeally circulating blood at a plurality of points in time series, evaluate the appropriateness of the hemodialysis treatment by evaluating whether the estimated dry weight approximates to the dry weight, and store a plurality of time series data when the hemodialysis treatment is found to be appropriate, they can be applied to other forms of apparatus and method for hemodialysis, such as an apparatus with other functions or without additional functions.

Obviously, numerous modifications and variations of the present invention are possible in light of the above teachings. It is therefore to be understood that within the scope of the appended claims, the invention may be practiced otherwise than as specifically described herein.

What is claimed is:

1. A hemodialysis apparatus comprising:
a dialysis device connecting with a dialyzer and an extracorporeal blood circuit, the dialysis device comprising an ultrafiltration apparatus and a dialysate supply;
a detecting device connected with a sensor, wherein the detecting device receives, from the sensor, periodic measurements of a parameter related to the concentration of the blood circulating extracorporeally, and calculates, using the periodic measurements, time series data representing a rate of change of circulating blood volume;
an evaluation device, connected with the detecting device, calculating time series data representing changes in plasma water index (PWI) during hemodialysis, based on a relation between a variation rate of circulating blood volume and a variation rate of a patient's body weight, using data including time series data received from the detecting device, and evaluating whether an estimated dry weight of a hemodialysis patient approximates to a calculated dry weight of the hemodialysis patient; and a memory device connected with the evaluation device and comprising a database, residing on a storage media, wherein the database contains a plurality of any of said time series data, wherein the evaluation device calculates the plasma water index (PWI) according to equation 1:

$$PWI = \frac{\Delta CPV\%}{\Delta BW\%}$$

wherein $\Delta CPV\%$ is the change in circulating blood plasma volume and $\Delta BW\%$ is a variation rate of the body weight.

2. The hemodialysis apparatus according to claim 1, further comprising:

a calculation device connected with the memory device and calculating an optimal change in selected time series data based on a corresponding plurality of time series data stored in the memory device.

3. The hemodialysis apparatus according to claim 2, wherein the calculation device calculates an optimal range, between a lower limit and an upper limit, corresponding to each periodic measurement of the parameter related to concentration of the blood circulating extracorporeally.

4. The hemodialysis apparatus according to claim 2, further comprising a display device, wherein the parameter measured by the detecting device is displayed in real time superimposed on a graph, and at least one of a change and a range of changes calculated by the calculation device is indicated.

5. The hemodialysis apparatus according to claim 2, further comprising a notification device, wherein a predetermined notification is provided when the parameter measured by the detecting device deviates from at least one of a change and a range of changes calculated by the calculation device.

6. The hemodialysis apparatus according to claim 1, wherein time series data stored in the memory device comprises universal time series data that are unrelated to specific conditions of a particular hemodialysis patients, and are standardized from selected time series data by performing a predetermined calculation.

7. The hemodialysis apparatus according to claim 1, wherein the sensor comprises a hematocrit sensor, $\Delta CPV\%$ is calculated according to equation 2:

$$\Delta CPV\% = \frac{\left(\frac{Ht1}{Ht2} - 1\right)}{\left(1 - \frac{Ht1}{100}\right)} * 100$$

and $\Delta BW\%$ is calculated according to equation 3:

$$\Delta BW\% = \frac{(-UFV)}{BW1} * 100$$

wherein Ht1 is a hematocrit value at the start of ultrafiltration, Ht2 is a hematocrit value at the end of ultrafiltration, UFV is a total ultrafilterated volume at the end of a hemodialysis treatment, and BW1 is a pretreatment body weight.

8. A system for analyzing a plasma water index (PWI) of a patient during hemodialysis comprising:

a dialysis device connecting with a dialyzer and an extracorporeal blood circuit, the dialysis device comprising an ultrafiltration apparatus and a dialysate supply;

a detecting device connected with a sensor, wherein the detecting device receives, from the sensor, periodic measurements of a parameter related to the concentration of the blood circulating extracorporeally, and calculates, using the periodic measurements, time series data representing a rate of change of circulating blood volume;

an evaluation device, connected with the detecting device, calculating time series data representing changes in the plasma water index (PWI) during hemodialysis, based on a relation between a variation rate of circulating blood volume and a variation rate of a patient's body weight, using data including time series data received from the detecting device, and evaluating whether an estimated dry weight of a hemodialysis patient approximates to a calculated dry weight of the hemodialysis patient; and a memory device connected with the evaluation device and comprising a database, residing on a storage media, wherein the database contains a plurality of any of said time series data, wherein the evaluation device calculates the plasma water index (PWI) according to equation 1:

$$PWI = \frac{\Delta CPV\%}{\Delta BW\%}$$

wherein $\Delta CPV\%$ is the change in circulating blood plasma volume and $\Delta BW\%$ is a variation rate of the body weight.

9. The system of claim 8, wherein the sensor comprises a hematocrit sensor, $\Delta CPV\%$ is calculated according to equation 2:

$$\Delta CPV\% = \frac{\left(\frac{Ht1}{Ht2} - 1\right)}{\left(1 - \frac{Ht1}{100}\right)} * 100$$

and $\Delta BW\%$ is calculated according to equation 3:

$$\Delta BW\% = \frac{(-UFV)}{BW1} * 100$$

wherein Ht1 is a hematocrit value at the start of ultrafitration, Ht2 is a hematocrit value at the end of ultrafiltration, UFV is a total ultrafilterated volume at the end of a hemodialysis treatment, and BW1 is a pretreatment body weight.

10. The hemodialysis apparatus according to claim 1, wherein time series data stored in the memory device comprises only the time series data where the estimated dry weight approximates to the calculated dry weight.

* * * * *